United States Patent
Markel et al.

(10) Patent No.: US 10,616,233 B1
(45) Date of Patent: Apr. 7, 2020

(54) METHOD FOR SECURELY LINKING HOSPITAL PATIENTS TO THEIR SERVICE PROVIDER ACCOUNTS

(71) Applicant: CSC Holdings, LLC, Bethpage, NY (US)

(72) Inventors: Robert Markel, Huntington, NY (US); Adam Labelson, Oyster Bay, NY (US)

(73) Assignee: CSC Holdings, LLC, Bethpage, NY (US)

( * ) Notice: Subject to any disclaimer, the term of this patent is extended or adjusted under 35 U.S.C. 154(b) by 478 days.

(21) Appl. No.: 15/205,369

(22) Filed: Jul. 8, 2016

Related U.S. Application Data

(63) Continuation of application No. 13/230,511, filed on Sep. 12, 2011, now Pat. No. 9,412,089.

(51) Int. Cl.
  *H04L 29/06* (2006.01)
  *G06F 19/00* (2018.01)
  *G16H 10/60* (2018.01)

(52) U.S. Cl.
  CPC ........ *H04L 63/102* (2013.01); *G06F 19/3418* (2013.01); *G06F 19/3456* (2013.01); *G06F 19/3481* (2013.01); *G16H 10/60* (2018.01); *H04L 63/083* (2013.01)

(58) Field of Classification Search
  CPC .... G05Q 50/24; H04N 21/472; H04N 21/278; H04N 21/8126
  See application file for complete search history.

(56) References Cited

U.S. PATENT DOCUMENTS

| | | | | |
|---|---|---|---|---|
| 5,867,821 A | * | 2/1999 | Ballantyne | G06Q 10/10 705/2 |
| 6,988,075 B1 | * | 1/2006 | Hacker | G06Q 10/10 705/3 |
| 7,185,282 B1 | * | 2/2007 | Naidoo | A61B 5/0002 348/E7.071 |
| 7,275,095 B1 | * | 9/2007 | Lebouill | H04L 12/2801 348/E7.061 |
| 7,707,599 B1 | * | 4/2010 | Groff | H04N 7/165 715/700 |
| 7,835,926 B1 | * | 11/2010 | Naidoo | A61B 5/0002 705/3 |
| 7,904,307 B2 | * | 3/2011 | Abolfathi | G06Q 30/06 705/2 |
| 7,996,244 B1 | * | 8/2011 | Fitch | G06Q 50/24 705/3 |
| 8,117,646 B2 | * | 2/2012 | Lorsch | G06Q 50/22 726/3 |
| 8,702,607 B2 | * | 4/2014 | LeBoeuf | G06F 19/00 600/301 |
| 9,412,089 B2 | * | 8/2016 | Markel | H04N 5/781 |
| 2002/0103675 A1 | | 8/2002 | Vanelli | |

(Continued)

*Primary Examiner* — Pankaj Kumar
*Assistant Examiner* — Timothy R Newlin
(74) *Attorney, Agent, or Firm* — Sterne, Kessler, Goldstein & Fox P.L.L.C.

(57) ABSTRACT

Methods and systems for linking a service provider account with patient care information are disclosed. A patient's account information is received. A service account for the patient is identified, and an association between a patient's care record and the service account is stored. Care information for the patient is received and transmitted to a device associated with the patient's service account.

21 Claims, 4 Drawing Sheets

(56) References Cited

U.S. PATENT DOCUMENTS

| | | | |
|---|---|---|---|
| 2002/0174344 A1* | 11/2002 | Ting | G06F 21/32 713/185 |
| 2002/0186243 A1* | 12/2002 | Ellis | G06F 19/3418 715/753 |
| 2002/0196141 A1* | 12/2002 | Boone | A61B 5/02055 340/540 |
| 2003/0177037 A1* | 9/2003 | Oka | G06F 19/324 705/2 |
| 2003/0212311 A1* | 11/2003 | Nova | A61N 1/37258 600/300 |
| 2005/0273817 A1* | 12/2005 | Rodriguez | G06F 3/0233 725/46 |
| 2007/0061393 A1* | 3/2007 | Moore | G06F 17/3089 709/201 |
| 2007/0162928 A1* | 7/2007 | Mickle | H04N 7/17318 725/37 |
| 2007/0299694 A1* | 12/2007 | Merck | G06Q 10/10 705/3 |
| 2008/0133273 A1* | 6/2008 | Marshall | G06Q 10/10 705/3 |
| 2008/0306771 A1* | 12/2008 | Zhou | G06Q 50/22 705/3 |
| 2009/0326979 A1* | 12/2009 | Ryan | G06F 19/3418 705/2 |
| 2010/0016683 A1* | 1/2010 | Lemmers | G06F 19/3418 600/301 |
| 2010/0017231 A1* | 1/2010 | Galbraith | G06Q 50/24 705/3 |
| 2010/0106519 A1* | 4/2010 | Lemke | G06F 19/3418 705/2 |
| 2010/0121156 A1* | 5/2010 | Yoo | G06F 19/3418 600/300 |
| 2010/0161352 A1* | 6/2010 | Lim | A61B 5/0002 705/3 |
| 2011/0090085 A1* | 4/2011 | Belz | G08B 21/0423 340/573.1 |
| 2011/0154419 A1* | 6/2011 | Kim | H04N 21/254 725/106 |
| 2011/0295617 A1* | 12/2011 | Berger | G06Q 10/10 705/3 |
| 2013/0067521 A1 | 3/2013 | Markel et al. | |
| 2013/0123068 A1* | 5/2013 | Sultan | A63B 24/0062 482/2 |
| 2013/0135115 A1* | 5/2013 | Johnson | G08C 19/00 340/870.02 |
| 2013/0172155 A1* | 7/2013 | Adamchick | A63B 71/0622 482/8 |

* cited by examiner

METHOD FOR SECURELY LINKING HOSPITAL PATIENTS TO THEIR SERVICE PROVIDER ACCOUNTS

CROSS-REFERENCE TO RELATED APPLICATIONS

The present application is a continuation of U.S. patent application Ser. No. 13/230,511, filed Sep. 12, 2011, now U.S. Pat. No. 9,412,089, which is incorporated herein by reference in its entirety.

BACKGROUND

Field

Embodiments relate to providing post-hospitalization patient care and information.

Background Art

Successful treatment of medical conditions that require hospitalization, often depends on the patient effectively complying with post-hospitalization medical directives. This is particularly true of certain chronic conditions, such as congestive heart failure. Hospitals and other patient care providers are increasingly subject to economic incentives to ensure that patients receive and follow post-hospitalization care. For example, under current legislation, a hospital may be responsible for costs if a patient is readmitted for the same condition within a defined period of time, such as 30 days after discharge. Accordingly, hospitals have strong incentives to deliver post-hospitalization follow-up care and services in an effective fashion, that patients will embrace and actually use.

What is needed is an easily accessible system for providing post-hospitalization care.

BRIEF DESCRIPTION OF THE DRAWINGS/FIGURES

Embodiments of the invention are described with reference to the accompanying drawings. In the drawings, like reference numbers may indicate identical or functionally similar elements. The drawing in which an element first appears is generally indicated by the left-most digit in the corresponding reference number.

DETAILED DESCRIPTION

While the present invention is described herein with reference to the illustrative embodiments for particular applications, it should be understood that the invention is not limited thereto. Those skilled in the art with access to the teachings provided herein will recognize additional modifications, applications, and embodiments within the scope thereof and additional fields in which the invention would be of significant utility.

In the detailed description of embodiments that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

The vast majority of individuals under hospitalization and the care of such professionals are older members of society. While these individuals may be familiar with televisions, they typically are not comfortable with the use of technology such as computers and the Internet.

As described above, post-hospitalization care is vital for the continued health of individuals after their discharge from a hospital. Patients' health may also be improved by greater access to health education related to their individual situations. Thus, making post-hospitalization care information and health education easily accessible to those patients who need it most may improve these individuals' health and reduce the need for additional hospitalization.

Environment

Figure 1:
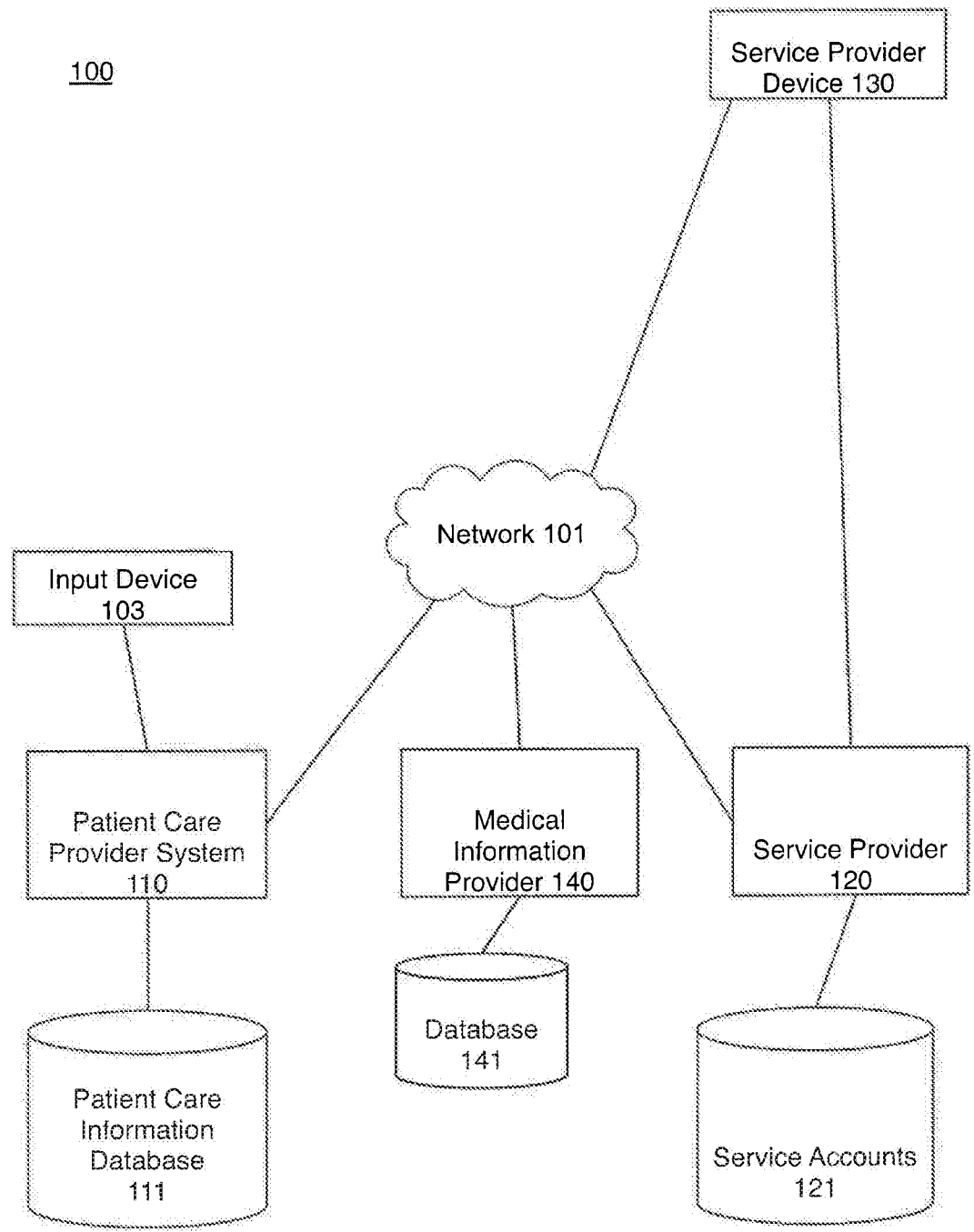
FIG. 1 is a diagram of an environment in accordance with one embodiment.

FIG. 1 is a diagram of an environment 100 that may be used in some embodiments disclosed herein. Environment 100 includes patient care provider system 110. Patient care provider system 110 may be a computing system used by, for example and without limitation, a hospital, a doctor's office, an outpatient facility, or another organization which treats patients. Patient care provider system 110 may further include, or be connected or coupled to, patient care information database 111. Patient care information database 111 may store patient care information, such as post-hospitalization care information, medical records, and other information. Patient care information database 111 may be implemented in any type of persistent memory, and may be a relational or a non-relational database.

Environment 100 further includes input device 103. Input device 103 may be used by a user, such as a patient of patient care provider 110. Input device 103 may be a set top box, cellular telephone, computer, television, or other device used by a patient to input information. Input device 103 may further be used by a nurse or other employee of a patient care provider. Further details of the interaction between input device 103 and patient care provider 110 will be explained herein.

Environment 100 further includes service provider 120. In one embodiment, service provider 120 is a cable television service provider. In other embodiments, service provider 120 may be a telephone service provider, cellular telephone service provider, satellite television service provider, internet-based television service provider, or other similar service provider.

Service provider 120 further includes service accounts 121. Service accounts 121 may be stored in a database or any other type of persistent memory. Service accounts 121 may include a plurality of service accounts for customers of the service provider 120. Each service account may include information related to the customers of the service provider 120, such as the name, address, telephone number, and other identifying information for customers.

Further, each service account 121 may be associated with one or more service provider devices 130. Service provider devices 130 may include cable television set-top boxes (STB), satellite television STBs, internet-based television STBs, cable modems, computing devices, cellular telephones, landline telephones, and other devices. Service provider devices 130 may be used by users, such as patients, after they have been discharged from a patient care provider facility. Service provider devices 130 may be connected to service provider 120 over a network, such as a wide area network, cellular network, other wireless network, or by coaxial cable, copper cable or other known method of connecting such devices. Service provider devices 130 may further be connected to network 101 using a wired or wireless connection.

Environment 100 may further include third party medical information provider 140. Third party medical information provider 140 may be connected to both service provider 120 and patient care provider 110, and may store an association between patient care records maintained by patient care provider 110 and service provider accounts stored by service provider 120.

Service provider 120, patient care provider system 110, and third party medical information provider 140 may be connected by way of network 101. Network 101 may be, for example and without limitation, a wide area network such as the Internet.

Method

Figure 2:
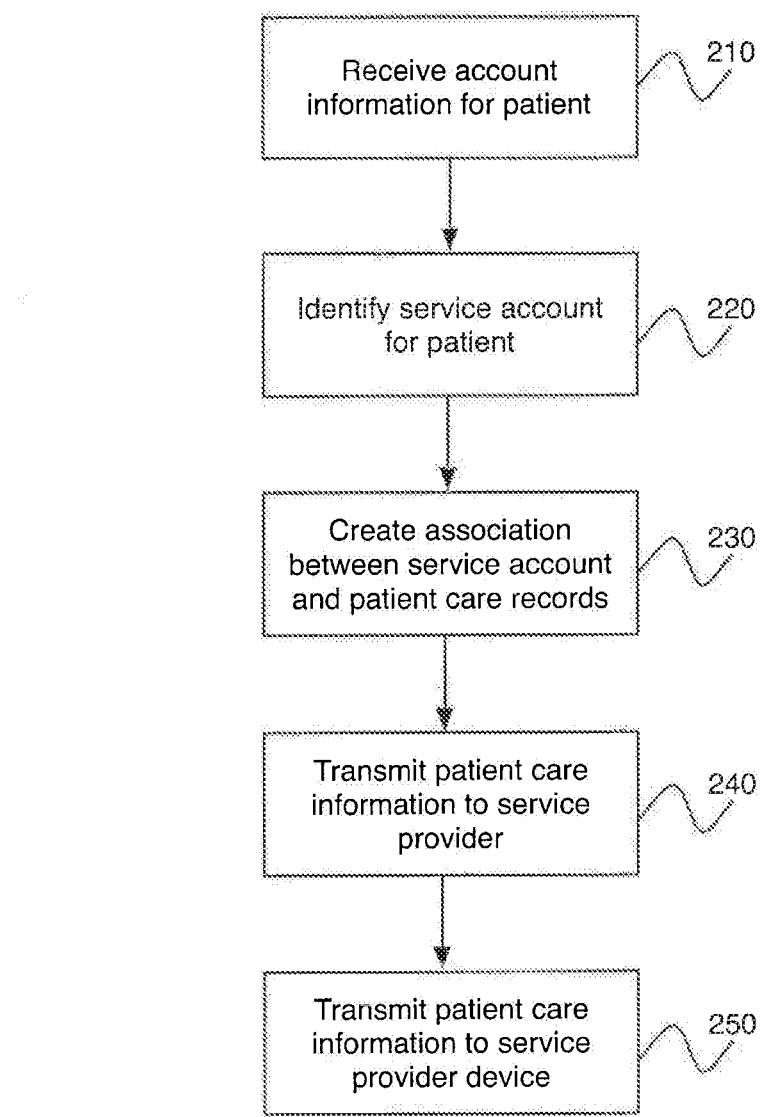
FIG. 2 is a flow diagram of a method in accordance with one embodiment.

To transmit care information to a service provider device 130, a service account 121 may be associated with a patient's hospital records or other medical care records. FIG. 2 is a flow diagram of a method 200 for transmitting care information to a patient's service provider device 130.

Method 200 begins at step 210. In step 210, account information for a patient is received. Account information may include, but is not limited to, a phone number, address, account number, name, social security number, or other identifying information. In one embodiment, account information is received by a patient care provider. For example, a patient may use an input device 103 to input her account information. In another embodiment, account information may be received by a patient care provider and transmitted to a service provider. In a further embodiment, account information may be received by a patient care provider and transmitted to a third party medical information provider.

In step 220, a service account for the patient associated with the account information is identified. For example, the service provider may be a cable television provider, and the service account may be the patient's cable television account with the provider. In one embodiment, the service provider may search its service accounts using the received account information and transmit an identification of the service account to a patient care provider or third party medical information provider. In another embodiment, an interface between a patient care provider and a service provider, or an interface between a third party medical information provider and a service provider, may allow the patient care provider or third party medical information provider to identify a service account for the patient associated with the account information.

In step 230, an association is created between the service account identified in step 220, and the patient's medical care records. The association may be created by the patient care provider 110, created by the service provider 120, or may be created by a third party medical information provider 140. In one embodiment, the association may be stored in a database along with the patient care information 111. In another embodiment, third party medical information provider 140 may store associations in a database 141.

In step 240, based on the association, patient care information is transmitted to and received by the service provider. In one embodiment, patient care information is transmitted from the patient care provider, such as a hospital or doctor's office, to the service provider. In another embodiment, patient care information is transmitted from a patient care provider to a third party medical information provider, and then to the service provider.

In step 250, patient care information is transmitted to a service provider device associated with the service account. For example, patient care information may be transmitted to a cable television set top box associated with the patient's service account. The patient care information may be accessed by a user through a healthcare application executing on the cable television set top box. In another embodiment, the patient care information may be accessed by a user through a healthcare application executing remotely, and accessible through the cable television set top box. The user of the service provider device may be the patient who entered the account information using, for example, input device 103 as described with reference to step 210. In one embodiment, patient care and other information may also be transmitted from a service provider device associated with the service account.

Example

Figure 3:
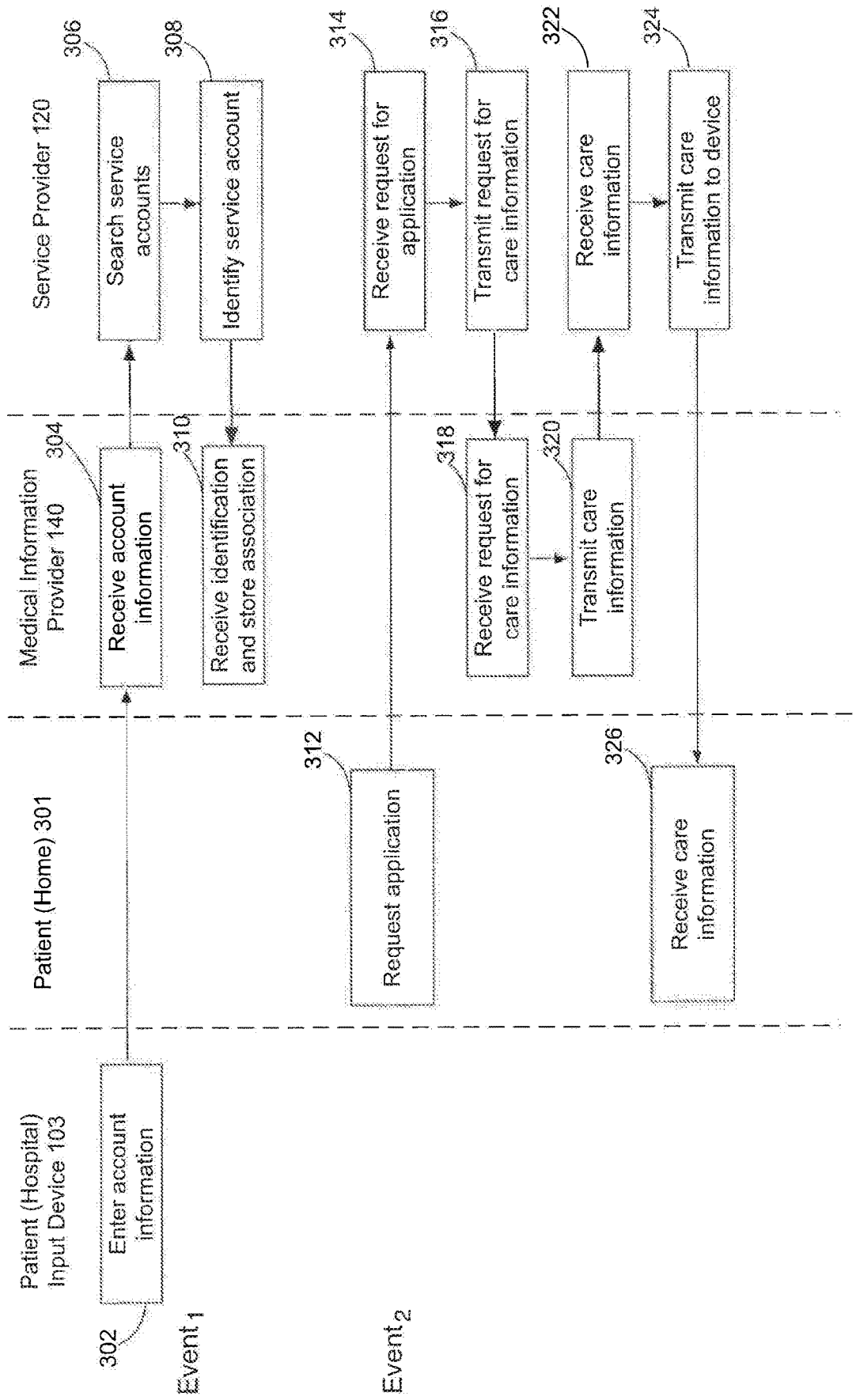
FIG. 3 is a swim lane diagram of an example timeline in accordance with one embodiment.

FIG. 3 is a swim lane diagram of an example timeline of events in accordance with one embodiment. During event $E_1$, a patient in a hospital may create an association between her care information, such as medical records, and a service account. As described below, the patient may create this association during discharge from a hospital. Thus, in box 302, the patient may use an input device 103 to enter her account information, such as a telephone number. At box 304, the third party medical information provider 140 may receive the account information, and transmit it to service provider 120. Service provider 120 may search its service accounts in box 306 to identify a service account inbox 308. The identification of the service account may be transmitted to third party medical information provider 310, which may also store an association between the patient's service account and care information.

During event $E_2$, after the patient has been discharged, the patient at home 301 may use a service provider device 130 associated with her account to request a healthcare application in box 312. In box 314, the service provider 120 may receive the request for the application, and transmit a request for care information in box 316. In box 318, the third party medical information provider 140 may receive the request for care information, and use the stored association to determine the care information to provide. For example, the third party medical information provider 140 may use the stored association to determine the care information that matches the service account which requested the healthcare application. In box 320, the third party medical information provider 140 may transmit the care information to service provider 120, which receives the care information in box 322. In box 324 then, the service provider 120 transmits the care information to a service provider device in the patient's home, which may receive the care information in box 326 and display the information to the user.

Additional Embodiments

In one embodiment, the patient may enter account information to create an association while being discharged from a patient care provider facility, such as a hospital. For example, a television terminal may be provided in the patient's room to enter account information and create an association such that the patient can receive post-hospitalization care and education from a service provider device associated with the patient's service account.

In another embodiment, the patient may associate a service provider account with medical records after discharge. For example, the service provider, third party medical information provider, or other entity, may provide the patient an opportunity to associate her service provider account with her medical records using an Internet-based application. Further, the service provider may provide the patient an opportunity to associate her service provider account with her medical records using an interactive application delivered via the service provider device, such as a set top box. In either example, the patient may use personal information, such as name, address, phone number, or other identifying information, to identify the service provider account, the patient's medical records and care information, or both.

In one embodiment, once a service account for the patient is identified, the patient may be asked to confirm that the service account is truly associated with the patient. In another embodiment, multiple service accounts for the patient may be identified using the account information. For example, if the patient has a common name, multiple service accounts may be identified for the patient if the patient enters her name as account information. The patient may be provided with a selection of multiple service accounts and may choose one to associate with her patient care records.

In one embodiment, while creating the association between the patient's medical records and the patient's service account information, the patient may be provided the option to add a password or personal identification number ("PIN") to the association. The password or PIN may be stored along with the association, and the user may be required to enter the password or PIN before she can access patient care information via the service provider device. Further, in one embodiment, the patient care information may not be transmitted to the service provider or to the service provider device until the correct password or PIN has been entered. The user may provide a password or PIN to a home caregiver such that the home caregiver can also access the information.

In some embodiments, the patient accesses her post-hospitalization care information via the service provider device. In one embodiment, if the service provider device is a television set top box, the patient may access the care information by tuning or setting the set top box to a specific channel that provides a healthcare application. In another embodiment, the patient may select a dedicated button on a remote control for the set top box to access the healthcare application. In yet a further embodiment, the set top box may be instructed to automatically access the healthcare application on a regular basis or at a specific time of day. In a further embodiment, the set top box may display a reminder to the user to access the healthcare information, or may deliver reminders of required actions (such as taking medication) if the user has not accessed the application.

In one embodiment, after an association is created, the association may be linked with a hardware address associated with a service provider device. For example, a service provider device may be associated with a unique Media Access Control address (MAC address). The association may be linked to the MAC address for the user's service provider device.

In one embodiment, the healthcare application may provide a survey to the patient on a periodic basis, such as a daily basis. The survey may ask the patient general information about her current health and condition. Additionally, the survey may confirm that the patient has taken her required medication. The responses to the survey may be communicated to a healthcare provider so that the healthcare provider can monitor the patient's health without an office visit.

Upon accessing the healthcare application, using the created association, the healthcare application may be interactive and customized to the particular follow-up care needs of the patient. If the association has been configured to require a password or PIN, the device or application may prompt the patient to enter their password or PIN in order to prove their identity before healthcare information may be presented.

The service provider device may be configured to allow multiple patients to access the healthcare application. In one embodiment, the service provider device may prompt each user for a password or PIN, and automatically retrieve the correct care information. In another embodiment, the healthcare application may require a user to select the desired patient, and then prompt the user for the appropriate password or PIN.

In one embodiment, the user may allow additional service provider accounts to be authorized to access the healthcare application on behalf of the patient. For example, a family member of the patient may be a caregiver to the patient in the family member's own home, instead of the patient's home. The patient may use the family member's information to create an association between the patient's records and the family member's service account information, to allow the family member to access the post-hospitalization care.

The healthcare application provided by the service provider device may provide a wide array of functionality to the patient and the healthcare provider. For example, the healthcare application may help a patient or her caregiver to manage medication information, including a detailed analysis of side effects and medication interaction. Further, the healthcare application may ensure that the patient is complying with the medication's dosing requirements and transmit such information to a caregiver or patient care provider. Additionally, the healthcare application may provide an interactive graphical user interface to allow the user to enter data associated with a medical condition.

The healthcare application may also interface with a variety of devices and technologies designed to manage and monitor various health conditions. For example, point-of-care monitoring devices, including, but not limited to, weight scales, glucose meters, implantable heart-health devices, and blood pressure monitors, may communicate with the healthcare application, which may transmit the patient's general health statistics to a patient care provider. Such systems may allow the patient care provider to intervene and modify treatment plans as necessary. Further, such a system may provide alerts to caregivers or other parties when health conditions decline. Connections between management and monitoring devices and the service provider device may be wired or wireless.

Other devices that may interact with the healthcare application may track the patient's compliance with various required follow-up healthcare actions. For example, a treadmill, exercise machine, or pedometer may communicate with the healthcare application to ensure the patient has completed her daily exercise. Similarly, the patient's medication bottles may be equipped with a sensor that can communicate with the health care application to determine if a patient has taken her medicine according to the dosing schedule. Connections between such compliance devices and the service provider device may be wired or wireless.

Further devices that may interact with the healthcare application may monitor the patient's general health. For example, bed sensors, toilet sensors, motion sensors, sound sensors, tilt sensors, water sensors, incontinence sensors, emergency call devices, cameras, and other sensors may all communicate with the health care application to allow the patient care provider or other interested parties to monitor the health of the patient.

The healthcare application may also provide testing for the patient's cognitive fitness. For example, the healthcare application may provide a thinking game or cognitive challenges to help older patients prevent or delay the onset of dementia or Alzheimer's disease.

The healthcare application may provide customized healthcare education to the patient. For example, if the patient suffers from migraines, the healthcare application may provide resources for avoiding situations where migraines could occur. Similarly, a patient with high cholesterol may be provided with recipes and other dietary information to help manage the patient's cholesterol level.

The healthcare application may further provide a facility for the patient to purchase various needed healthcare items. For example, the healthcare application may provide an interface between the patient and a pharmacy, where the pharmacy can receive notification from the patient that a refill is needed. Further, the healthcare application may provide an interface between the patient and a drugstore, to allow the patient to purchase various other items, such as over-the-counter medication, and medical supplies. The healthcare application may also provide an interface between the patient and her patient care provider, such as a doctor, who may then communicate the patient's needed items to the pharmacy or drugstore.

The healthcare application may further allow the patient care provider to send a customized post-discharge schedule of care to the patient's service provider device. For example, the patient care provider may have the ability to send a variety of coordinated, automated messages to the patient at an appropriate time, proactively inviting the patient to learn more about her care, condition, and safety, as well as other aspects of her post-discharge care.

The healthcare application may further allow the patient to communicate with a doctor or other patient care provider through the application interface. The healthcare application may intelligently route such a request for information or contact, which may allow the healthcare provider to offer a better customer experience.

In embodiments, transmission of medical records data is compliant with various state and federal regulations, such as the Health Insurance Portability and Accountability Act (HIPAA). Further, the patient care provider or third party medical information provider, prior to transmission of patient care information or medical records to the service provider, may encrypt data to be transmitted. In one embodiment, data may be transmitted and used without any personally identifying information. Medical records data may then be decrypted by the service provider device upon receipt of the data. The service provider may be unable to view or decrypt the patient care information or medical records to preserve confidentiality. The patient may specify a password, key, or other mechanism to encrypt and decrypt her medical records data such that the information is not intercepted during transmission.

Although certain embodiments are described with reference to television set top boxes, embodiments may be implemented with non-television devices, such as cellular telephones. Certain cellular telephones, including smartphones and other devices, allow users to run applications that can be automatically installed and activated upon creation of an association between a patient's medical records and her service account.

Figure 4:
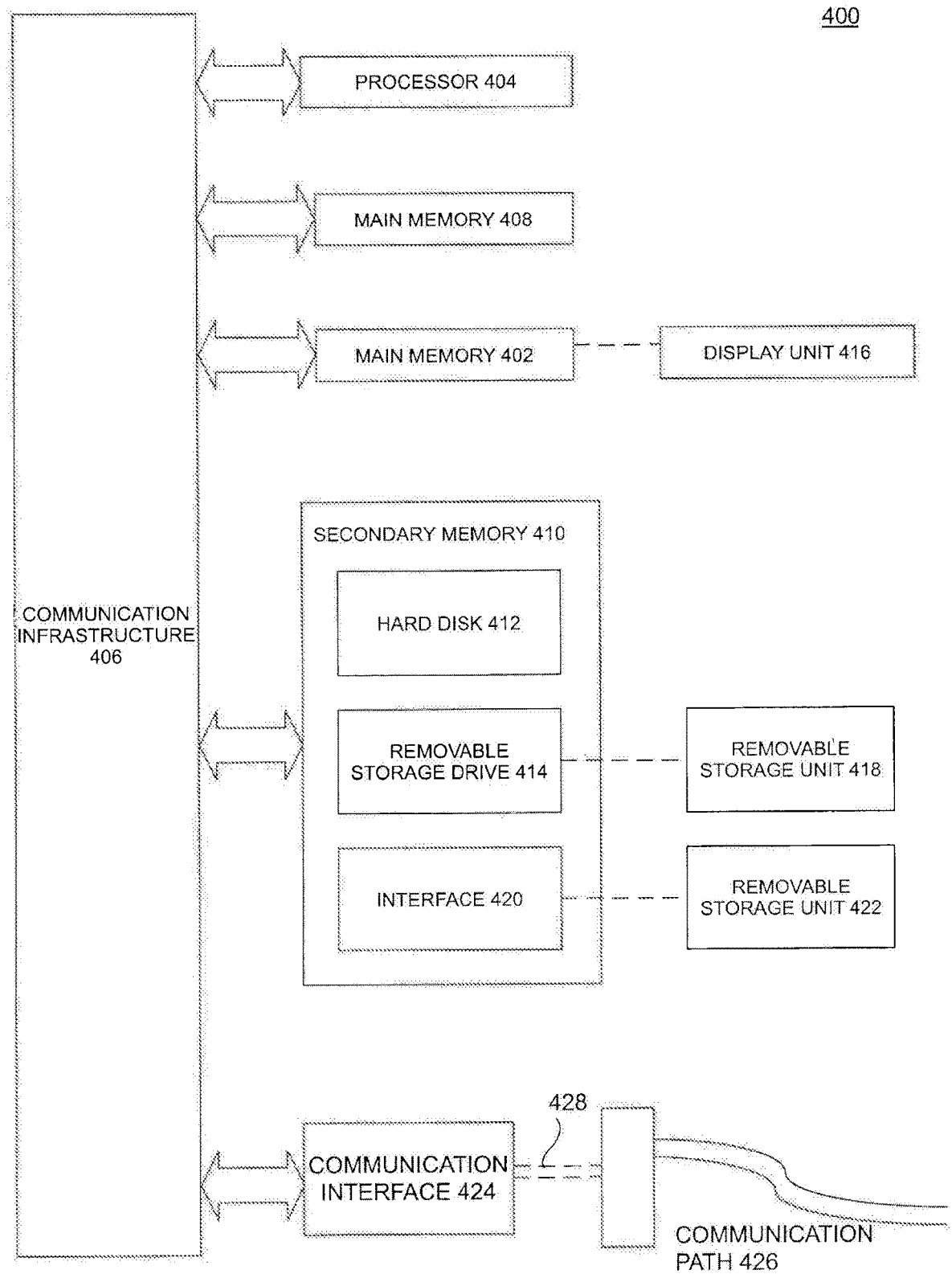
FIG. 4 is a diagram of an example computer system that can be used in embodiments.

Various aspects described herein can be implemented by software, firmware, hardware, or a combination thereof. FIG. 4 illustrates an example computer system 400 in which the embodiments, or portions thereof, can be implemented as computer-readable code. For example, the functions of patient care provider system 110, medical information provider system 140, service provider 120, or service provider device 130 can be implemented in system 400. Various embodiments disclosed herein are described in terms of this example computer system 400.

Computer system 400 includes one or more processors, such as processor 404. Processor 404 is connected to a communication infrastructure 406 (for example, a bus or network).

Computer system 400 also includes a main memory 408, preferably random access memory (RAM), and may also include a secondary memory 410. In accordance with implementations, user interface data may be stored, for example and without limitation, in main memory 408. Secondary memory 410 may include, for example, a hard disk drive and/or a removable storage drive. Removable storage drive 414 may include a floppy disk drive, a magnetic tape drive, an optical disk drive, a flash memory, or the like. The removable storage drive 414 reads from and/or writes to removable storage unit 418 in a well-known manner. Removable storage unit 418 may include a floppy disk, magnetic tape, optical disk, etc. which is read by and written to by removable storage drive 414. As will be appreciated by persons skilled in the relevant art(s), removable storage unit 418 includes a computer readable storage medium having stored therein computer software and/or data.

Computer system 400 may also include a main memory 402. Main memory 402 may include, for example, cache, and/or static and/or dynamic RAM. Main memory 402 may be separate from main memory 408 or may be a part thereof. Main memory 402 may be adapted to communicate with display unit 416. Display unit 416 may comprise a computer monitor or similar means for displaying graphics, text, and other data received from main memory 402. In alternative implementations, secondary memory 410 may include other similar means for allowing computer programs or other instructions to be loaded into computer system 400. Such means may include, for example, a removable storage unit 422 and an interface 420. Examples of such means may include a program cartridge and cartridge interface (such as that found in video game devices), a removable memory chip (such as an EPROM, or PROM) and associated socket, and other removable storage units 422 and interfaces 420 which allow software and data to be transferred from the removable storage unit 422 to computer system 400.

Computer system 400 may also include a communications interface 424. Communications interface 424 allows software and data to be transferred between computer system 400 and external devices. Communications interface 424 may include a modem, a network interface (such as an Ethernet card), a communications port, a PCMCIA slot and card, or the like. Software and data transferred via communications interface 424 are in the form of signals which may be electronic, electromagnetic, optical, or other signals capable of being received by communications interface 424. These signals are provided to communications interface 424 via a communications path 426. Communications path 426 carries signals and may be implemented using wire or cable, fiber optics, a phone line, a cellular phone link, an RF link or other communications channels.

In this document, the term "computer readable storage medium" is used to generally refer to media such as removable storage unit 418, removable storage unit 422, and a hard disk installed in hard disk drive 412. Computer readable storage medium can also refer to one or more memories, such as main memory 408 and secondary memory 410, which can be memory semiconductors (e.g. DRAMs, etc.). These computer program products are means for providing software to computer system 400.

Computer programs (also called computer control logic) are stored in main memory 408 and/or secondary memory 410. Computer programs may also be received via communications interface 424 and stored on main memory 408 and/or secondary memory 410. Such computer programs, when executed, enable computer system 400 to implement the implementations as discussed herein. In particular, the computer programs, when executed, enable processor 404 to implement the processes of the present disclosure, such as the steps in the methods discussed above. Accordingly, such computer programs represent controllers of the computer system 400. Where implementations use software, the software may be stored in a computer program product and loaded into computer system 400 using removable storage drive 414, interface 420, or hard drive 412.

Embodiments may be directed to computer program products comprising software stored on any computer readable medium. Such software, when executed in one or more data processing device, causes a data processing device(s) to operate as described herein. Embodiments may employ any computer useable or readable medium. Examples of non-transitory computer readable storage media include, but are not limited to, primary storage devices (e.g., any type of random access memory), and secondary storage devices (e.g., hard drives, floppy disks, CD ROMS, ZIP disks, tapes, magnetic storage devices, and optical storage devices, MEMS, nano-technological storage device, etc.). Other computer readable media include communication mediums (e.g., wired and wireless communications networks, local area networks, wide area networks, intranets, etc.).

Embodiments may be implemented in hardware, software, firmware, or a combination thereof. Embodiments may be implemented via a set of programs running in parallel on multiple machines.

The summary and abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

What is claimed is:

1. A television service provider device, the television service provider device being coupled to a television service provider that is coupled to a patient care provider system at a patient care facility, the television service provider device comprising:
    a memory that stores a healthcare application;
    a processor configured to execute the healthcare application to allow a user of the television service provider device to access patient care information that is received from the patient care provider system via the television service provider and associated with a television service account of the user that is maintained by the television service provider for providing television services to the television service provider device, the healthcare application, when executed by the processor, configuring the processor to:
        transmit a health statistic of the user that is received from a point-of-care monitoring device to the television service provider for transmission to the patient care provider system,
        access the patient care information relating to the health statistic of the user that is received from the patient care provider system via the television service provider, and
        provide an interface for the user to purchase a healthcare item relating to the patient care information.

2. The television service provider device of claim 1, wherein the television service provider device comprises:
    a cable television set-top box (STB);
    a satellite television STB;
    an internet-based television STB;
    a cable modem;
    a computing device;
    a cellular telephone; or
    a landline telephone.

3. The television service provider device of claim 1, wherein the processor is further configured to request the healthcare application from the television service provider.

4. The television service provider device of claim 1, wherein the healthcare application, when executed by the processor, further configures the processor to:
    create an association between the patient care information and the television service account after the user has been discharged from the patient care facility.

5. The television service provider device of claim 4, wherein the processor is further configured to execute an interactive application, the interactive application when executed by the processor, configuring the processor to allow the user to associate the television service account with the patient care information.

6. The television service provider device of claim 1, wherein the healthcare application, when executed by the processor, further configures the processor to receive the patient care information from a third party medical information provider via the television service provider.

7. The television service provider device of claim 4, wherein the memory is further configured to store a password or personal identification number ("PIN") to the association; and
　　wherein the healthcare application, when executed by the processor, further configures the processor to:
　　　　compare a password or a PIN entered by the user with the stored password or the stored PIN, and
　　　　allow the user to access the patient care information when the entered password or the entered PIN matches the stored password or the stored PIN.

8. The television service provider device of claim 1, wherein the healthcare application, when executed by the processor, further configures the processor to deliver a reminder of a required action as determined by the patient care information to the user if the user has not accessed the healthcare application.

9. The television service provider device of claim 1, wherein the healthcare application, when executed by the processor, further configures the processor to assist the user to manage information relating to a medication from the patient care information.

10. The television service provider device of claim 1, wherein the point-of-care monitoring device comprises:
　　a weight scales;
　　a glucose meter;
　　an implantable heart-health device; or
　　a blood pressure monitor.

11. The television service provider device of claim 1, wherein the healthcare application, when executed by the processor, further configures the processor to interact with an exercise device to track compliance of the user with an exercise routine of the patient care information.

12. The television service provider device of claim 1, wherein the interface comprises:
　　an interface between the user and a pharmacy;
　　an interface between the user and a drugstore; or
　　an interface between the user and the patient care facility.

13. The television service provider device of claim 1, wherein the healthcare application, when executed by the processor, further configures the processor to establish a communication between the user and the patient care provider system.

14. A method for operating a television service provider device, the television service provider device being coupled to a television service provider that is coupled to a patient care provider system, the method comprising:
　　storing, by the television service provider device, a healthcare application;
　　executing, by the television service provider device, the healthcare application to allow a user of the television service provider device to access patient care information that is received from the patient care provider system via the television service provider and associated with a service account of the user that is maintained by the television service provider for providing television services to the television service provider device, the executing comprising:
　　　　transmitting a health statistic of the user that is received from a point-of-care monitoring device to the television service provider for transmission to the patient care provider system,
　　　　accessing the patient care information relating to the health statistic of the user that is received from the patient care provider system via the television service provider, and
　　　　providing an interface for the user to purchase a healthcare item relating to the patient care information.

15. The method of claim 14, further comprising:
　　requesting the healthcare application from the television service provider.

16. The method of claim 14, further comprising:
　　storing a password or personal identification number ("PIN") to an association between the patient care information and the television service amount;
　　comparing a password or a PIN entered by the user with the stored password or the stored PIN, and
　　allowing the user to the access patient care information when the entered password or the entered PIN matches the stored password or the stored PIN.

17. The method of claim 14, further comprising:
　　delivering a reminder of a required action as determined by the patient care information to the user if the user has not accessed the healthcare application.

18. The method of claim 14, wherein executing further comprises:
　　assisting the user to manage information relating to a medication from the patient care information.

19. The method of claim 14, wherein the point-of-care monitoring device comprises:
　　a weight scales;
　　a glucose meter;
　　an implantable heart-health device; or
　　a blood pressure monitor.

20. The method of claim 14, wherein executing further comprises:
　　interacting with an exercise device to track compliance of the user with an exercise routine of the patient care information.

21. The method of claim 14, wherein executing further comprises:
　　establishing a communication between the user and the patient care provider system.

* * * * *